(12) United States Patent
Wong et al.

(10) Patent No.: US 8,158,367 B2
(45) Date of Patent: Apr. 17, 2012

(54) CANCER DIAGNOSIS BASED ON LEVELS OF ANTIBODIES AGAINST GLOBO H AND ITS FRAGMENTS

(75) Inventors: Chi-Huey Wong, Taipei (TW); Chung-Yi Wu, Taipei (TW); Cheng-Chi Wang, Taipei (TW); Alice L. Yu, Taipei (TW)

(73) Assignee: Academia Sinica, Taipei (TW)

( * ) Notice: Subject to any disclaimer, the term of this patent is extended or adjusted under 35 U.S.C. 154(b) by 60 days.

(21) Appl. No.: 12/485,516

(22) Filed: Jun. 16, 2009

(65) Prior Publication Data
US 2009/0317837 A1 Dec. 24, 2009

Related U.S. Application Data

(60) Provisional application No. 61/061,974, filed on Jun. 16, 2008.

(51) Int. Cl.
*G01N 33/53* (2006.01)
(52) U.S. Cl. ...................................................... 435/7.1
(58) Field of Classification Search .................. None
See application file for complete search history.

(56) References Cited

U.S. PATENT DOCUMENTS

2002/0006629 A1* 1/2002 Danishefsky et al. ....... 435/7.23
2006/0269979 A1* 11/2006 Dwek et al. .................... 435/23
2009/0162405 A1* 6/2009 Qian ........................... 424/277.1

FOREIGN PATENT DOCUMENTS

| JP | 2002-515060 | 5/2002 |
| WO | WO 2006/068758 | 6/2006 |
| WO | WO2010/005735 | 1/2010 |

OTHER PUBLICATIONS

Van Slambrouk et al. "Clustering of monosialyl-Gb5 initiates downstream signaling events leading to invasion of MCF-7 breast cancer cells," The Biochemical Journal, 401(3):689-699 (2007).
Kannagi et al., "New globoseries glycosphingolipids in human teratocarcinoma reactive with the monoclonal antibody directed to a developmentally regulated antigen, stage-specific embryonic antigen 3," The Journal of Biological Chemistry, 258(14):8934-8942 (2005).
Liang et al., "Glycan Arrays: Biological and Medical Applications," Current Opinion in Chemical Biology, 12:86-92 (2008).
Huang et al., "Carbohydrate Microarray for Profiling the Antibodies Interacting with Globo H Tumor Antigen," PNAS, 103(1):15-20 (2006).
Wang et al., "Glycan Microarray of Globo H and Related Structures for Quantitative Analysis of Breast Cancer," PNAS, 105(33):11661-11666 (2008).

* cited by examiner

*Primary Examiner* — Hong Sang
(74) *Attorney, Agent, or Firm* — Occhiuti Rohlicek & Tsao LLP

(57) ABSTRACT

A cancer diagnostic method using a glycan array that contains Gb5 and Globo H, Bb2, Bb3, and/or Bb4.

21 Claims, 2 Drawing Sheets

CANCER DIAGNOSIS BASED ON LEVELS OF ANTIBODIES AGAINST GLOBO H AND ITS FRAGMENTS

RELATED APPLICATION

This application claims priority to U.S. Provisional Application No. 61/061,974, filed on Jun. 16, 2008, the content of which is hereby incorporated by reference in its entirety.

BACKGROUND OF THE INVENTION

Globo H, containing a hexasaccharide epitope, is expressed in various cancers, as well as in normal epithelial cells and glandular tissues. See Huang et al., *Proc. Natl. Acad. Sci. USA* 103:15-20 (2006), Wang et al., *Proc. Natl. Acad. Sci. USA* 33:11661-11666 (2008), and Chang et al., *Proc. Natl. Acad. Sci. USA* 33:11667-11672 (2008). It has been reported that sera from breast cancer patients contain high levels of anti-Globo H antibodies. However, the level of these antibodies alone is not a reliable indication of breast cancer.

SUMMARY OF THE INVENTION

The present invention is based on an unexpected discovery that the ratio of the level of antibodies against Globo H, its fragment Bb2, Bb3, or Bb4, to the level of antibodies against Gb5, another fragment of Globo H, is significantly higher in breast cancer patients than in cancer-free humans.

Accordingly, this invention features a cancer diagnostic method, including (i) providing a sample (e.g., a serum sample) containing antibodies from a subject (e.g., a human) who is suspected of having a cancer (e.g., breast cancer, melanoma, neuroblastoma, skin cancer, liver cancer, prostate cancer, ovary cancer, colon cancer, stomach cancer, lung cancer, and pancreas cancer), (ii) incubating the sample with Gb5 and one or more of Globo H, Bb2, Bb3, and Bb4 to allow binding of these molecules to antibodies in the sample, (iii) measuring both the amount of Gb5-bound antibodies and the amount of Globo H-bound, Bb2-bound, Bb3-bound, or Bb4-bound antibodies, and (iv) determining whether the subject has the cancer based on the ratio of the amount of Globo H-bound, Bb2-bound, Bb3-bound, or Bb4-bound antibodies to the amount of Gb5-bound antibodies. A higher ratio indicates that the subject has the cancer. Globo H, Gb5, Bb2, Bb3, and Bb4 can be immobilized on a supporter device to form a glycan array. In one example, the array contains Gb5 and one of Globo H, Bb2, Bb3, and Bb4. In another example, it contains all of these molecules.

Also within the scope of this invention is use of Gb5 and one or more of Globo H, Bb2, Bb3, and Bb4 for cancer diagnosis and for the manufacture of a medical device used in cancer diagnosis.

The details of one or more examples of the invention are set forth in the description below. Other features or advantages of the present invention will be apparent from the following drawings and detailed description of several examples and also from the appended claims.

BRIEF DESCRIPTION OF THE DRAWINGS

The drawings are first described.

DETAILED DESCRIPTION OF THE INVENTION

We have discovered that the level ratio of anti-Globo H/anti-Gb5, anti-Bb2/anti-Gb5, anti-Bb3/anti-Gb5, or anti-Bb4/anti-Gb5 antibodies is significantly higher in breast cancer patients than in cancer-free individuals. Thus, any of these ratios serves as a reliable indication in cancer diagnosis.

Accordingly, described herein is a method of diagnosing cancer by detecting the amounts of antibodies against Gb5 and one or more of Globo H, Bb2, Bb3, Bb4 in a subject suspected of having cancer, e.g., a human who is genetically susceptible to cancer, and determining whether the subject has cancer based on any of the level ratios mentioned above. The antibodies mentioned above can be IgG, IgM, IgE, IgA, or IgD, or a mixture thereof.

Figure 1:
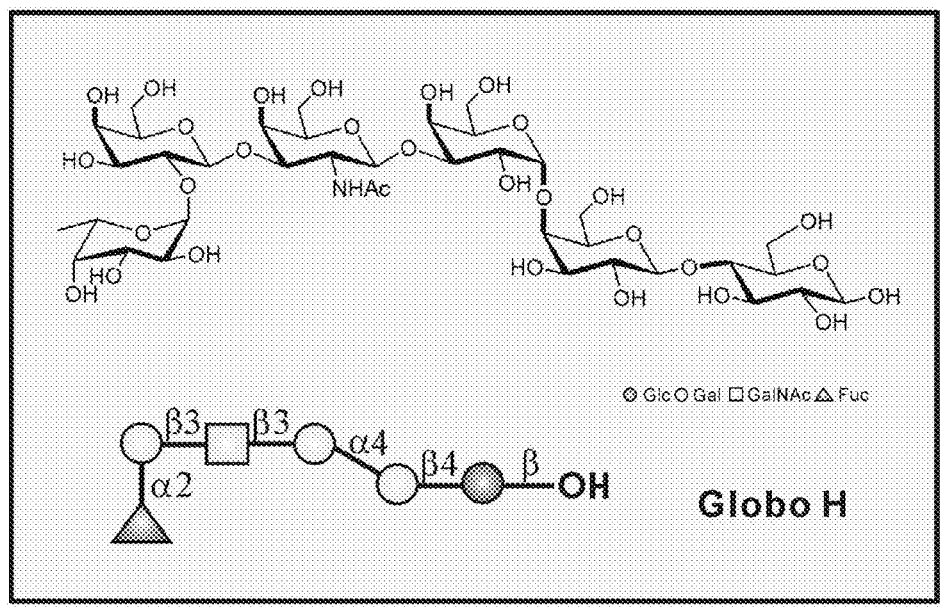
FIG. 1 is a diagram depicting the structures of the hexasaccharide epitope in Glogo H (GH) and fragments of this epitope. Panel A: the structure of the hexasaccharide epitope. Panel B: the structures of the hexasaccharide epitopes and its seven fragments.
Figure 1:
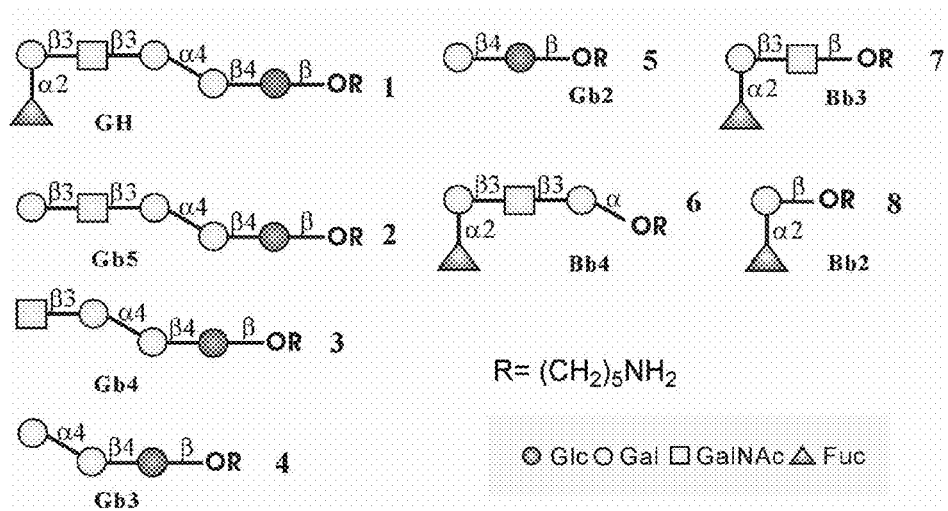
Figure 2:
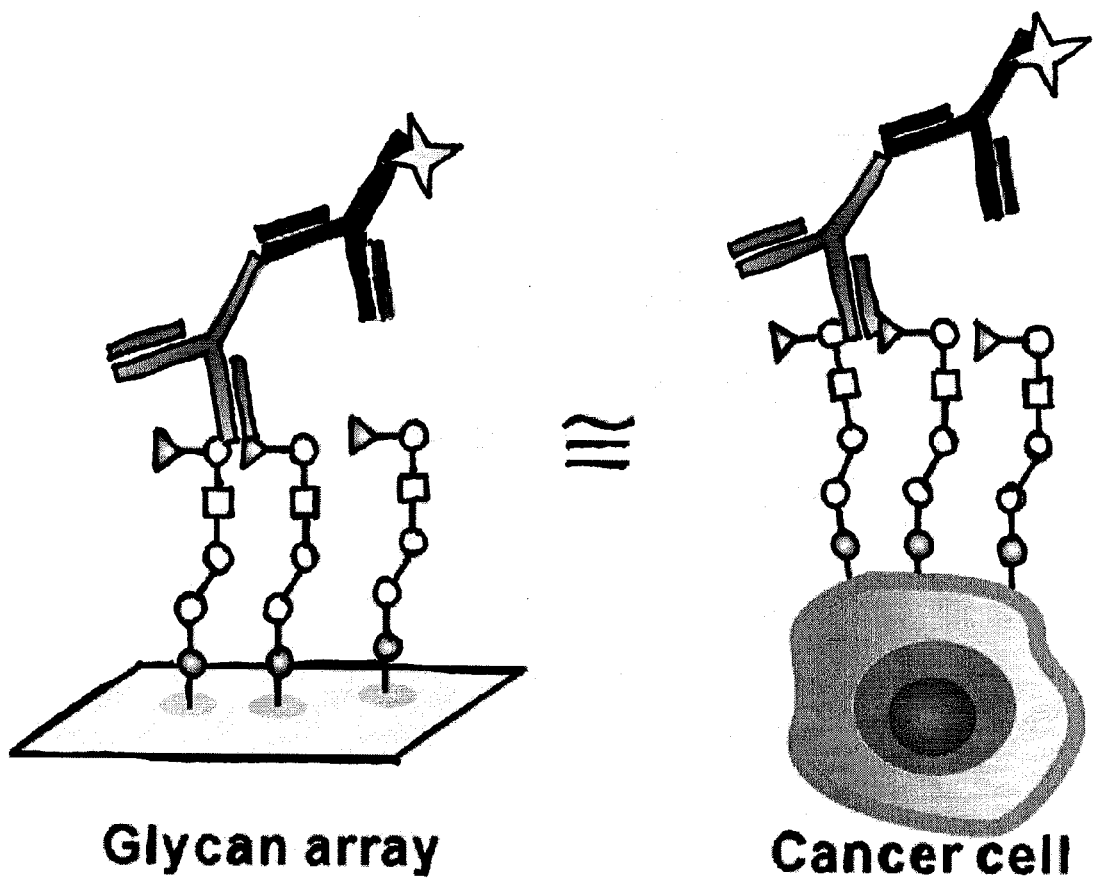
FIG. 2 is a diagram showing use of glycan array, which mimics cancer cell surface, for detecting anti-glycan antibodies.

Globo H is a glycan containing the hexasaccharide epitope shown in FIG. 1, Panel A, and, optionally, a non-sugar moiety. Its fragment (e.g., Gb5, Bb2, Bb3, and Bb4) is a glycan containing a fragment of the hexasaccharide epitope and if applicable, the non-sugar moiety. Seven fragments of the hexasaccharide epitope are shown in FIG. 1, Panel B. These oligosaccharides can be prepared by routine methods. See, e.g., Huang et al., *Proc. Natl. Acad. Sci. USA* 103:15-20 (2006). Preferably, they are conjugated with a non-sugar linker such as an alkylamine, e.g., $(CH_2)_5NH_2$, or an alkylazide, e.g., $(CH_2)_5N_3$, which can be covalently bonded to a supporting device (e.g., a polymer substrate) made of various materials, such as glass, plastic, nylon, metal, or silicon. Each of Globo H, Gb5, Bb2, Bb3, and Bb4 can be spotted at a defined address on the supporting device so as to form a glycan array. This array, mimicking the surface of a cancer cell that expresses the oligosaccharide epitopes contained in Globo H, Gb5, Bb2, Bb3, and Bb4 (see FIG. 2), can be used to detect the levels of antibodies that bind to the oligosaccharide epitopes.

To perform the method of this invention, the glycan array described herein is incubated with an antibody-containing sample from a subject suspected of having a cancer. Examples of the sample include, but are not limited to, sera, saliva and lymph node fluids. The array is washed to remove unbound antibodies and then incubated with a labeled secondary antibody that specifically bind to the antibodies of interest, which can be human IgG, IgA, IgD, IgE, or IgM. The glycan array is washed again to remove unbound secondary antibody molecules and the intensities of the signal released from the bound secondary antibody molecules correspond to the levels of the target antibodies. When a higher level ratio of anti-Globo H/anti-Gb5, anti-Bb2/anti-Gb5, anti-Bb3/anti-Gb5, or anti-Bb4/anti-Gb5 is observed in a subject, the subject is diagnosed as having of the cancer or at risk for developing the cancer.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Binding of Antibodies Vk9, Mbr1, and A488 to a Glycan Array

Oligosaccharides Globo H, Gb5, Gb4, Gb3, Gb2, Bb4, Bb3, Bb2 shown in FIG. 1 were prepared according to the one-pot programmable protocol described in Hung et al., *Proc. Natl. Acad. Sci. USA* 103-15-20 (2006). These oligosaccharides were covalently attached onto a NHS-coated glass slide, which was purchased from Nexterion H slide (SCHOTT North America), by the standard microarray robotic printing technology described in Hung et al. and Blixt et al., *Proc. Natl. Acad. Sci. USA* 101:17033-17038 (2004). More specifically, an aliquot from a stock solution (80 μM) of each oligosaccharide was placed on the glass slide in 16-row format, two rows for each oligosaccharide.

The following three antibodies were used in this study:
Mbr1, a mouse IgM anti-Globo H monoclonal antibody,
VK-9, a mouse IgG anti-Globo H monoclonal antibody, and
A488, anti-mouse/human Gb5 monoclonal antibody.

Each of the antibodies was incubated with the glass slide (to which the oligosaccharides attached) described above in 0.05% Tween 20/PBS buffer (pH 7.4) in a humidifying chamber with shaking for 1 h. The slide was then washed, in turn, three times with 0.05% Tween 20/PBS buffer (pH 7.4), three times with PBS buffer (pH 7.4), and three times with water. Next, the slide was incubated with Cy3-conjugated goat anti-mouse IgM (for MBr1) or IgG (for VK-9 and A488) antibody in the same chamber with shaking for 1 h. The slide was again washed three times with 0.05% Tween 20/PBS buffer (pH 7.4), three times with PBS buffer (pH 7.4), and three times with $H_2O$ and dried. Finally, the slide was scanned at 595 nm (for Cy3-conjugated secondary antibody) and 488 nm (for A488 anti-SSEA-3 antigen antibody) using a microarray fluorescence chip reader (ArrayWorx microarray reader).

All of the three antibodies bound to the glycan array described above. VK9 specifically bound to Globo H and Bb4; Mbr1 specifically bound to Globo H and BB4 and also bound to Bb3 at a lower affinity; and A488 specifically bound to Gb5. These results indicate that the glycan array is capable of capturing antibodies that bind to Globo H and/or its fragments.

EXAMPLE 2

Use of a Glycan Array for Detecting Antibodies Against Globo H and its Fragments in Breast Cancer Patients Plasma samples from breast cancer patients and healthy individuals were diluted 1:20 with 0.05% Tween 20/3% BSA/PBS buffer (pH 7.4) and incubated with the glycan array slide described in Example 1 above in a humidifying chamber with shaking for 1 h. After being washed with 0.05% Tween 20/PBS buffer (pH 7.4), PBS buffer (pH 7.4), and water, each for three times, the slide was incubated with Cy3-conjugated goat anti-human IgM or IgG antibody in the humidifying chamber with shaking for 1 h. The slide was then washed three times with 0.05% Tween 20/PBS buffer (pH 7.4), three times with PBS buffer (pH 7.4), and three times with $H_2O$. After being dried, the slide was scanned at 595 nm (for Cy3-conjugated secondary antibody) with a microarray fluorescence chip reader (ArrayWorx microarray reader).

As shown in Tables 1 and 2 below, the level ratios of Globo H-bound IgG/Gb5-bound IgG (GH/Gb5 IgG) and Globo H-bound IgM/Gb5-bound IgM (GH/Gb5 IgM) were much higher in the plasma samples of the breast cancer patients then in the plasma samples of the healthy individuals. As also shown in the two tables, the ratios of Bb2/Gb5 IgG, Bb4/Gb5 IgM, Bb3/Gb5 IgM, and Bb2/Gb5 IgM of the cancer patients were significantly higher than those of the healthy individuals. These data indicate that the above listed ratios are reliable markers for diagnosing cancer.

TABLE 1

IgG level ratios of Globo H and its fragments Bb2, Bb3, and Bb4 to Gb5 in breast cancer patients (n = 58) and healthy individuals (n = 47)

| | GH/Gb5 | | Bb4/Gb5 | | Bb3/Gb5 | | Bb2/Gb5 | |
|---|---|---|---|---|---|---|---|---|
| IgG ratio % | Healthy | Cancer | Healthy | Cancer | Healthy | Cancer | Healthy | Cancer |
| Mean | 26.92 | 58.31 | 11.91 | 17.84 | 15.22 | 22.54 | 78.02 | 120.8 |
| SD | 18.49 | 31.14 | 20.54 | 19.6 | 23.12 | 23.22 | 63.63 | 92.26 |
| P | $p < 0.0001$*** | | $p < 0.1360$ | | $p < 0.1106$ | | $p < 0.0063$** | |

***$p < 0.001$, extremely significant;
**$p = 0.001-0.01$, very significant

TABLE 2

IgM level ratios of Globo H and its fragments Bb2, Bb3, and Bb4 to Gb5 in breast cancer patients (n = 57) and healthy individuals (n = 47)

| | GH/Gb5 | | Bb4/Gb5 | | Bb3/Gb5 | | Bb2/Gb5 | |
|---|---|---|---|---|---|---|---|---|
| IgM ratio % | Healthy | Cancer | Healthy | Cancer | Healthy | Cancer | Healthy | Cancer |
| Mean | 27.82 | 53.98 | 15.73 | 22.74 | 15.36 | 40.51 | 16.19 | 30.36 |
| SD | 23.42 | 35.41 | 21.60 | 23.98 | 23.30 | 59.76 | 18.83 | 35.44 |
| P | $p < 0.0001$*** | | $P < 0.1259$* | | $p < 0.0043$** | | $p < 0.0105$* | |

***$p < 0.001$, extremely significant;
**$p = 0.001-0.01$, very significant
*$p = 0.01-0.05$, significant

EXAMPLE 3

Use of Glycan Array for Monitoring Immune Responses Induced by Globo H Vaccine Mice (6-week-old female BALB/c mice, BioLASCO, Taiwan) were immunized subcutaneously with the Globo H-KLH vaccine (Optimer Pharmaceuticals, Inc., San Diego, Calif.) once every week for three weeks. Control mice were injected with phosphate buffer saline (PBS). Serum samples were collected from the treated mice 10 days after the last immunization. These samples were subjected to serial dilution at 30, 120, 240, 480, 960, and 1920 folds and the titers of anti-Globo H antibodies were examined in the diluted serum samples using the glycan array slide described in Example 1 above ($3.5 \times 10^{-14}$ mol of oligosaccharides per spot) or by conventional ELISA (coated with $1.28 \times 10^{-10}$ mol of Globo H per well).

The Globo H-KLH vaccine induced secretion of anti-Globo H antibodies in the immunized mice. See Table 3 below. It has also been found that the glycan array assay described above is much more sensitive as compared with conventional ELISA.

TABLE 3

Immune Response Induced by Globo H Vaccine Determined by Glycan Array Analysis and ELISA

| Dilution Fold | Increased Immune Response* | |
|---|---|---|
| | Glycan Array Assay | ELISA |
| 30 | 374.7 ± 87.83 | 4.01 ± 1.58 |
| 120 | 188.4 ± 78.93 | 1.92 ± 0.75 |
| 240 | 102.2 ± 44.21 | 1.08 ± 0.48 |
| 480 | 44.86 ± 17.05 | 0.20 ± 0.10 |
| 960 | 12.13 ± 4.08 | 0.30 ± 0.14 |
| 1,920 | 3.203 ± 1.048 | ND |

*Calculated as follows: (post-immune signal intensity − pre-immune signal intensity)/background signal intensity

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A cancer diagnostic method, comprising
providing a sample containing antibodies from a subject suspected of having cancer,
incubating the sample with Gb5 and one or more of Globo H, Bb2, Bb3, and Bb4 to allow binding of antibodies in the sample to the Gb5 and the one or more of Globo H, Bb2, Bb3, and Bb4,
measuring both the amount of Gb5-bound antibodies and the amount of Globo H-bound, Bb2-bound, Bb3-bound, or Bb4-bound antibodies, and
determining whether the subject has the cancer based on the amounts of all of the bound antibodies,
wherein the cancer is both Globo H-positive and Gb5-positive; and a higher ratio of the amount of Globo H-bound, Bb2-bound, Bb3-bound, or Bb4-bound antibodies to the amount of Gb5-bound antibodies, as compared with that of a cancer-free subject, indicates that the subject has the cancer.

2. The method of claim 1, wherein the incubating step is performed by mixing the sample with Gb5 and Globo H.

3. The method of claim 1, wherein the incubating step is performed by mixing the sample with Gb5 and Bb3.

4. The method of claim 1, wherein the incubating step is performed by mixing the sample with Gb5 and Bb2.

5. The method of claim 1, wherein the incubating step is performed by mixing the sample with Gb5, Globo H, Bb2, Bb3, and Bb4.

6. The method of claim 1, wherein the sample is serum, saliva, or lymph node fluid.

7. The method of claim 1, wherein the Gb5 and the one or more of Globo H, Bb2, Bb3, and Bb4 are immobilized on a supporting device.

8. The method of claim 1, wherein the cancer is selected from the group consisting of breast cancer, skin cancer, liver cancer, prostate cancer, ovary cancer, colon cancer, stomach cancer, lung cancer, and pancreas cancer.

9. The method of claim 8, wherein the cancer is breast cancer.

10. The method of claim 9, wherein the Gb5 and the one or more of Globo H, Bb2, Bb3, and Bb4 are immobilized on a supporting device.

11. The method of claim 9, wherein the incubating step is performed by mixing the sample with Gb5 and Globo H.

12. The method of claim 11, wherein the Gb5 and the Globo H are immobilized on a supporting device.

13. The method of claim 9, wherein the incubating step is performed by mixing the sample with Gb5 and Bb2.

14. The method of claim 9, wherein the incubating step is performed by mixing the sample with Gb5 and Bb3.

15. The method of claim 9, wherein the incubating step is performed by mixing the sample with Gb5, Globo H, Bb2, Bb3, and Bb4.

16. The method of claim 9, wherein the sample is serum, saliva, or lymph node fluid.

17. The method of claim 16, wherein the sample is serum.

18. The method of claim 6, wherein the sample is serum.

19. The method of claim 1, wherein the cancer is an epithelial cancer.

20. The method of claim 1, wherein the antibodies measured are IgG antibodies.

21. The method of claim 1, wherein the antibodies measured are IgM antibodies.

* * * * *